United States Patent [19]

Birkmayer et al.

[11] Patent Number: 4,970,200
[45] Date of Patent: Nov. 13, 1990

[54] AGENT FOR TREATMENT OF PARKINSON'S DISEASE

[75] Inventors: Walther Birkmayer; Jörg Birkmayer, both of Wien, Austria; Reinhard Horowski, Berlin, Fed. Rep. of Germany; Helmut Wachtel, Berlin, Fed. Rep. of Germany; Peter-Andreas Löschmann, Berlin, Fed. Rep. of Germany

[73] Assignee: Schering Aktiengesellschaft, Berlin and Bergkamen, Fed. Rep. of Germany

[21] Appl. No.: 317,545

[22] Filed: Mar. 1, 1989

[30] Foreign Application Priority Data

Mar. 1, 1988 [DE] Fed. Rep. of Germany ....... 3807003
Mar. 15, 1988 [DE] Fed. Rep. of Germany ....... 3809024

[51] Int. Cl.[5] .................. A61K 31/455; A61K 31/70; C07H 19/207
[52] U.S. Cl. .................................... 514/52; 424/94.1; 424/94.4
[58] Field of Search ................. 514/52; 424/94.4, 94.1

[56] References Cited

U.S. PATENT DOCUMENTS 3,326,756  6/1967  O'Hollaren ..................... 424/94.1
3,341,412  9/1967  O'Hollaren et al. ............. 424/94.1

OTHER PUBLICATIONS

Birkmayer, W. J., Neuro-Visceral Relations, vol. 31, suppl. IX, pp. 297–308 (1969).
Birkmayer, W., et al., Archiv für Psychiatrie und Zeitschrift F. D. Ges. Neurologie, vol. 210, No. 1, pp. 29–35 (1967).
Ramsey, R., et al., BBRC, vol. 135, No. 1, 26, pp. 269–275 (1986).
Blair, J. et al., The Lancet 1 (8369), p. 167 (1984).
Grisham, M. et al., J. Neurochem. 49, No. 1, pp. 876–882 (1987).
Singer, T. P. et al., J. Neurochem., vol. 49, No. 1, pp. 1–8 (1987).
Birkmayer, W., et al., Ann. Clin. Lab. Sci., vol. 19, No. 1, pp. 38–43 (1989).

Primary Examiner—Johnnie R. Brown
Assistant Examiner—Gary L. Kunz
Attorney, Agent, or Firm—Millen, White & Zelano

[57] ABSTRACT

The enzyme cofactor nicotinamide adenine dinucleotide or a salt thereof is useful for the treatment of Parkinson's disease.

20 Claims, No Drawings

AGENT FOR TREATMENT OF PARKINSON'S DISEASE

BACKGROUND OF THE INVENTION

Parkinson's disease is caused by a disturbed dopaminergic neurotransmission in the basal ganglia, generally as a result of increasing destruction of dopaminergic neurons, occurring first in the substantia nigra, and subsequently over the course of the disease in other areas as well. In advanced cases, an increasing lack of noradrenaline (e.g., in the locus caeruleus) has been shown. Even in the early stages of the disease, a very clear decrease in tyrosine hydroxylase activity is also seen; it is interesting that this enzyme activity is also greatly reduced in other systems and organs (e.g., in the adrenal medulla) (see table 3 of Birkmayer and Riederer, Parkinson's Disease, second edition, page 34, Springer Verlag Vienna 1985, reproduced below as Table 1).

TABLE 1

| Brain Areas | Tyrosine Hydroxylase in Various Brain Areas in Parkinson's Disease | | |
|---|---|---|---|
| | | Control | Parkinsonian |
| N. caudatus | (15) | 27.8 ± 2.3 | 3.5 ± 1.0 (6)* |
| Puramen | (5) | 16.2 ± 5.9 | 1.2 ± 0.4 (6)* |
| S. nigra | (4) | 19.4 ± 6.2 | 4.9 ± 1.8 (4)* |
| L. caeruleus | (4) | 3.3 ± 0.1 | 2.0 ± 0.6 (2) |
| N. ruber | (5) | 5.7 ± 1.9 | 2.1 ± 1.4 (3) |
| Raphe + R.F. | (4) | 0.9 ± 0.6 | 1.5 ± 0.4 (5) |
| Hypothalamus | (5) | 3.1 ± 1.0 | 1.5 ± 0.3 (3) |
| C. mamillare | (5) | 0.6 ± 0.4 | 0.5 ± 0.9 (2) |
| N. accumbens | (5) | 2.0 ± 0.7 | 2.7 ± 2.2 (3) |
| Adrenal medulla | (5) | 186.2 ± 5.5 | 49.7 ± 12.4 (4) |

Number of patients in parentheses. Mean value ± sem (nmole) Dopa/g-tissue hour)
*p<0.01.

In conventional therapy, the missing or reduced dopaminergic activity is replaced by the dopamine precursor L-DOPA; when this effect decreases, the L-DOPA effect can be increased further by specific suppression of the enzyme monoamine oxidase (MAO-8), which breaks down the dopamine.

But after years of use these treatment strategies-although the life expectancy of the patients was improved—often led to severe and unpredictable fluctuations in mobility (fluctuations, on-off phenomena), which appreciably impair the patients' quality of life. These fluctuations can be prevented or at least reduced partially by timely use of post-synaptic agonists such as lisuride.

It has been suggested that the sudden reduction in mobility is related to a temporary depletion of tyrosine hydrolylase (Birkmayer and Riederer, Parkinson's Disease, second edition, page 81, Springer Verlag, Vienna, 1985). However, an increased load of tyrosine hydroxylase can also be postulated, based on the biochemistry of some of the standard therapies.

SUMMARY OF THE INVENTION

It can be assumed that, under normal conditions, this key enzyme of dopamine (and noradrenaline) synthesis is sufficiently induced and is supplied with cofactors. But with Parkinson's disease, a mistake in the control of the synthesis of tyrosine hydroxylase may be involved as a cause.

Clinical tests have surprisingly shown that even with patients with advanced Parkinson's disease and severe fluctuations in mobility, the administration of the enzyme cofactor, e.g., NADH, which is required for tyrosine hydroxylase activity, causes dramatic improvement in the motor system without requiring the addition of p-tyrosine.

Thus, this invention provides the use of nicotinamide adenine dinucleotide (in reduced (NADH) or unreduced (AND) form) or a salt thereof for treatment of Parkinsonism.

The clinical results are represented in the following table based on the example of three persons suffering from Parkinson's disease.

TABLE 2

| Age (years) | | Disability |
|---|---|---|
| 73 | duration of disease - 9 years without therapy | 75% |
| | 25 mg of NADH in 250 ml of NaCl 0.9% i.v., daily from 11/30 to 12/19/87 (in hospital) | 20% |
| | Madopar ®[1] 62.5 mg 2 times daily from 12/19/87 to 1/4/88 (at home) | 50–60% |
| | With the addition of 50 mg of NADH slowly i.v., once weekly to the basic therapy of 2 × 62.5 mg Madopar ® (at home) (observed until 1/25/88) | 30% |
| 59 | duration of disease - 8 years previous therapy 3 × ½ tab Sinemet ®[2] 3 × 1 | 60% |
| | 11/2/87–11/14/87 3 × ½ tab Sinemet ® Jumex ®[3] 1 tablet Jatrosom ®[4] 1 tablet + 50 mg of NADH daily | 30% in "on" |
| | Fixing of the NADH inf. 1 × weekly | 20%, "off" times became shorter |
| 62 | duration of disease - 8 years 2/19/86 with 3 × 125 mg Madopar ® 2 tab Jumex ® Saroten ®[5] 2 mg until 11/2/86 decline to | 40% |
| | with 2 ampules of oxiferiscorbone 2 ampules/d Madopar ® 3 × 125 mg Artane ®[6] 2 × 2 mg after 3 weeks, improvement to | 60% |
| | 8/28/87 prostate operation 9/20/87 with 3 × 250 mg of Madopar ® 2 × 1 tab Jumex ® 250 mg of tryptophan | 30% |
| | in addition, 50 mg of NADH 2 × weekly i.v. | 20% (on)/ 60% (off) |
| | without NADH | 40% (on)/ 80% (off) |
| | 2/10/88 2 × 250 mg of Madopar ® 2 × 1 tab Jumex ® 10 mg Saroten ® and 2 × weekly 50 mg of NADH i.v. | 20–30%(on) 60–70%(off) |

[1]Levodopa, Benserazide
[2]Carbidopa, Levodopa
[3]Deprenyl
[4]Tranylcyprominsulfate, Trifluoperacin-HCl
[5]Amitriptyline-HCl
[6]Trihexyphenidil-HCl The data of table 2 demonstrate that the ingestion of NADH or a salt thereof leads to a significant improvement of the disability. This is established both in the on and in the off phases and is achieved both with simultaneous administration of standard preparations, especially L-DOPA, and without simultaneous administration of known Parkinsonian active agents. A shortening of the off phase is also achieved with the medication according to the invention.

For use according to the invention, the coenzyme NAD or NADH or a phusiologically acceptable salt thereof can be formulated in the standard way with pharmaceutically acceptable inactive ingredients and carriers. Optionally, NADH or NAD can also be used in combination with other anti-Parkinsonism therapies and other Parkinsonian active ingredients and co-agents—for example, post-synaptic dopaminergic agonists such as lisuride, apomorphine or other anti-Parkinsonian agents like amantadine, deprenyl and central anticholinergics (Y. Goodman and Gilman's: The Pharmacological Basis of Therapeutics, Chapter 21 Drugs for Parkinson's Disease, Spasticity and Acute Muscle Spasm, 7th Edition MacMillan Publishing Company, New York, pp. 473-486, 1985).

All of the foregoing agents which per se are useful to treat Parkinsonism or which in combination with other drugs, e.g., L-DOPA, are useful to treat Parkinsonism, are used in accordance with this invention in their normal therapeutic regimens; where an alleviation of dosage or frequency of administration is possible in view of the advantages provided by this invention, suitable modifications can be routinely determined using fully conventional procedures, e.g., testing via conventional Parkinsonism protocols, e.g., analogous to the clinical tests described above or as discussed in the literature, e.g., in Goodman and Gilman.

For use as a pharmaceutical agent, NADH and NAD can be incorporated in standard galenic formulations for oral, parenteral (such as intravenous or subcutaneous) or sublingual use. The production of a particular pharmaceutical agent is performed in ways known in the art, e.g., by the active ingredient being processed with carriers, diluents and taste corrigents, etc., common in galenic pharmacy. The preparations can be present in solid form as tablets, capsules, coated tablets or in liquid form as solutions, suspensions, sprays or emulsions as well as formulations with delayed release or active ingredients.

A suitable single dose for parenteral application is 5 to 500 mg, preferably 25 to and 100 mg and the daily dose is 5 to 1,500 mg, preferably 25 to 300 mg, e.g., to improve the motor system in Parkinsonian patients. Suitable oral doses are in the same range as for parenteral administration, or can optionally be up to 1,000% higher.

Suitable physiologically acceptable salts of the coenzyme NADH or NAD include all known physiologically acceptable acidic and basic salt-forming substances, for example: inorganic acids such as, for example, hydrohalic acids, sulfuric acid, phosphoric acid; organic acids such as, for example, aliphatic or aromatic carboxylic acids, e.g., formic acid, acetic acid, succinic acid, lactic acid, malic acid, tartaric acid, citric acid, maleic acid, phenylacetic acid, benzoic acid, salicylic acid or ascorbic acid; or alkali metal hydroxides or alkaline earth metal hydroxides or salts.

The entire texts of all applications, patents and publications, if any, cited above and below, and of West German Application P 38 07 003.0 and West German Application P 38 09 024.4, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising (a) NADH or NAD or a pharmaceutically acceptable salt thereof, (b) an amount of another anti-Parkinsonian ingredient, and (c) a pharmaceutically acceptable carrier, and essentially no p-tyrosine.

2. A composition of claim 1, wherein the amount of NADH or NAD is 5 mg to 500 mg.

3. A composition of claim 1, wherein the amount of NADH or NAD is 25 mg to 100 mg.

4. A composition of claim 2, wherein said carrier is adapted for parenteral administration.

5. A composition of claim 2, wherein said carrier is adapted for oral administration.

6. A composition of claim 1, adapted for oral administration and wherein the amount of NADH or NAD is 5 mg to 5,000 mg.

7. A composition of claim 1, wherein the other Parkinsonian active agent is L-DOPA.

8. A composition of claim 1, wherein the other Parkinsonian active agent is lisuride.

9. A composition of claim 1, wherein the other Parkinsonian active ingredient is a post-synaptic dopaminergic agonist.

10. A composition of claim 1, wherein the other Parkinsonian active agent is a monoamine oxidase inhibitor.

11. A composition of claim 1, wherein the other Parkinsonian active agent is apomorphine.

12. A method of treating Parkinson's disease, comprising administering to a host in need thereof an effective amount of nicotinamide adenine dinucleotide (NADH or NAD), without administration of p-tyrosine to said host.

13. A method of claim 12, wherein the daily dosage for parenteral or oral administration is 5 mg to 1,500 mg.

14. A method of claim 13, Wherein the daily dosage is 25 to 300 mg.

15. A method of claim 13, wherein the unit dosage is 5 mg to 500 mg.

16. A method of claim 12, wherein the daily dosage for oral administration is up to 15,000 mg.

17. A method of claim 12, further comprising administering an effective amount of another anti-Parkinsonism ingredient.

18. A method of claim 17, wherein said other agent is L-DOPA.

19. A method of claim 17, wherein said other agent is a monoamine oxidase inhibitor or a post-synaptic dopaminergic agent.

20. A method of claim 17, wherein said other ingredient is simultaneously coadministered.

* * * * *